United States Patent [19]

Sturtzkopf et al.

[11] Patent Number: 5,026,372
[45] Date of Patent: Jun. 25, 1991

[54] FIXATION DEVICE FOR THE EXTERNAL ADJUSTING OF BONE FRAGMENTS

[76] Inventors: Robert Sturtzkopf, Wilhelm-Hey-Strasse 14, 8000 Munich 40; Hans-Werner Stedtfeld, Schlossweiherstrasse 43, 8500 Nuremberg, both of Fed. Rep. of Germany

[21] Appl. No.: 266,809

[22] Filed: Nov. 3, 1988

[30] Foreign Application Priority Data

Nov. 5, 1987 [DE] Fed. Rep. of Germany ....... 3737617
Nov. 2, 1988 [DE] Fed. Rep. of Germany ....... 3837228

[51] Int. Cl.⁵ ............................................. A61F 5/04
[52] U.S. Cl. ...................................... 606/54; 606/59; 606/105
[58] Field of Search ................................. 606/53–59, 606/105

[56] References Cited

U.S. PATENT DOCUMENTS

| | | | |
|---|---|---|---|
| 3,709,219 | 1/1973 | Halloran | 606/105 |
| 4,102,339 | 7/1978 | Weber et al. | 606/105 |
| 4,600,000 | 7/1986 | Edwards | 606/54 |
| 4,621,627 | 11/1986 | DeBastiani et al. | 128/92 Z X |
| 4,628,922 | 12/1986 | Dewar | 606/59 X |
| 4,714,076 | 12/1987 | Comte et al. | 128/92 ZW |
| 4,745,913 | 5/1988 | Castaman et al. | 182/92 Z X |

FOREIGN PATENT DOCUMENTS 0011258 11/1979 Fed. Rep. of Germany .
3543042 6/1987 Fed. Rep. of Germany .

Primary Examiner—Robert A. Hafer
Assistant Examiner—Kerry Owens
Attorney, Agent, or Firm—Harness, Dickey & Pierce

[57] ABSTRACT

The invention relates to a fixation device for externally adjusting bone fragments. A pair of members anchored to the bone fragments are connected to each other to allow a longitudinal displacement of the fixing unit. According to the invention the connection of the members is defined by a hinge configuration which allows guiding and aligning both members when the fixing unit is released for stimulating the healing process. A bracket is mounted on a parallelogram hinge to generate a pressure or, respectively, a tension force to move the bone fragments apart or draw them together. According to the invention the hinge configuration comprises telescopic members centered by spring means.

16 Claims, 4 Drawing Sheets

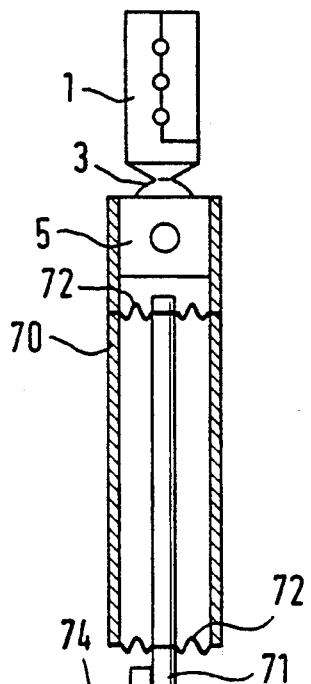
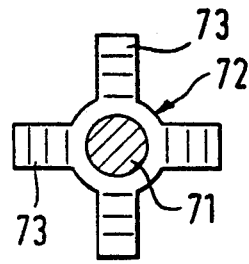
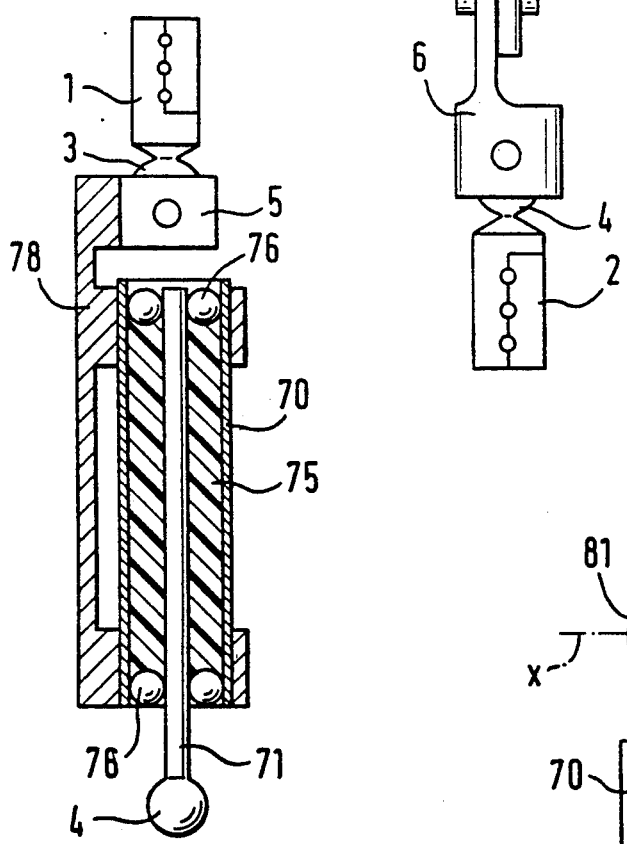
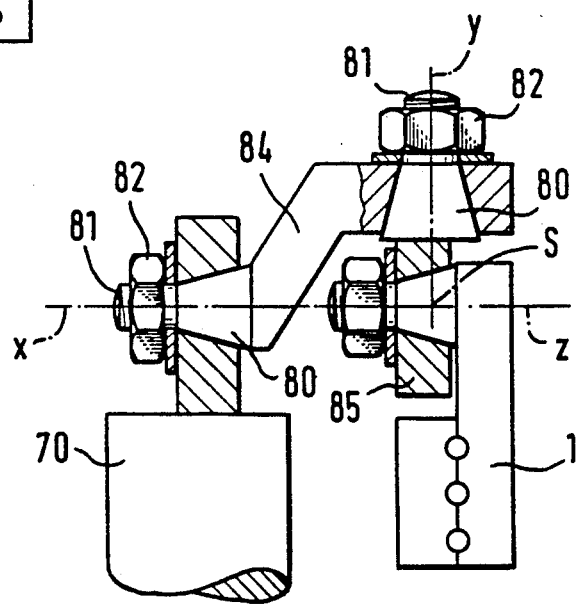

FIXATION DEVICE FOR THE EXTERNAL ADJUSTING OF BONE FRAGMENTS

BACKGROUND OF THE INVENTION

The present invention relates generally to orthopaedic devices and more particularly to a device for externally fixing a pair of bones.

A known fixation unit (German application 37 37 617.9) comprises a column-shaped guiding member slidably disposed in a sleeve. A screw mounted in the sleeve engages a longitudinal groove in the guiding member to prevent rotating and to adjust the length of the fixation unit. Each member of the unit is connected through a ball joint to a clamping means which is secured to each bone fragment by a number of threaded bolts. The fixation unit allows one to adjust both bone fragments with respect to each other and to fixedly maintain the fragments in their position, while directing all forces, to which the fragments are subjected, to the fixation unit thereby relieving the fracture.

As healing occurs, a connective tissue initially grows in the fracture gap between the bone fragments until the gap is finally filled out by bone substance. It is beneficial to the healing process to release the fixation unit after some time and compress the fracture by applying a load. It has been shown that the growing of bone substance in the fracture gap may be delayed leaving the fracture flexible when the fracture is not loaded.

The approach of the bone fragments after releasing the fixation device to narrow the fracture gap can be measured by a travel measuring system of known type which is attached to both telescopic members. It should be understood that the travel distance to be measured is rather small lying in the range of at most several millimeters. The compression measured provides valuable information with respect to the healing process.

A substantial drawback of previous fixation devices is jamming. Therefore it has been proposed to improve the friction characteristics between the telescopic members by a layer of extremely hard material (German 37 22 595). While it was possible to substantially improve the sliding characteristics, there remain other disadvantages to the guidance of the members when the fixing unit is released. In particular the telescopic members can rotate with respect to each other by applying even light forces. Additionally, bending forces may occur preventing a reliable measure of the compression of the bone fragments.

SUMMARY OF THE INVENTION

It is the main object of the present invention to provide an improved fixation device. In particular, any jamming of the fixing unit should be avoided.

A further object is to provide a structure in which the sliding motion of both members of the unit is proportional to the load applied.

A still further object is to provide an improved guiding means to prevent undesired motions of the bone fragments when the unit is disengaged.

According to the invention both members of a fixation unit for externally fixing a pair of bone fragments are connected to each other through a parallelogram hinge. The hinge connects both members, which extend parallel to each other, by two pairs of pivotal links.

This results in practically friction-free motion of the fixing unit in the longitudinal direction. Both elements are safely guided free of play. Rotating of both elements with respect to each other is prevented. The hinge has a relatively small stroke under load in the range of several millimeters or even less.

According to a particularly preferred embodiment of the invention an adjusting means is provided which engages the links of the hinge and pivots the hinge to increase or decrease the length of the hinge. It is thus possible to apply a tension or a compression to the bone fragments to vary the gap between them. By applying a tension force to draw the bone fragments together or by applying a compressive force to push the bone fragments away from each other, the healing process is improved or the broken bones are lengthened, respectively.

In a still further embodiment of the invention the force applied to the bone fragments by the bracket is measured or respectively limited to a predetermined value.

According to a still further embodiment of the invention, the fixation device is centered in a neutral position by spring means so that any longitudinal displacement either extending or compressing the device is against the spring force. It has been found that this is particularly beneficial for the patient. In a first embodiment the hinge is provided with blade springs or, respectively, the links of the hinge are replaced by blade springs.

In a further embodiment the hinge includes a pair of elements which are connected to each other by spring means to allow for longitudinal motion and prevent radial displacement.

In a still further embodiment mechanical springs are replaced by an elastomeric material. In a preferred embodiment the elements are provided in a telescopic configuration.

According to the invention the fixation device is mounted through a pair of multiple pivoting adjusting means to the bone fragments.

BRIEF DESCRIPTION OF THE DRAWINGS

FIG. 8 is a section view of another fixation device of the invention, FIG. 9 is a plan view of a blade spring used in the embodiment of FIG. 8, FIG. 10 is a section view of still another embodiment of the invention, and FIG. 11 is a section view of a multiple pivoting joint.

DESCRIPTION OF THE PREFERRED EMBODIMENT

Figure 1:
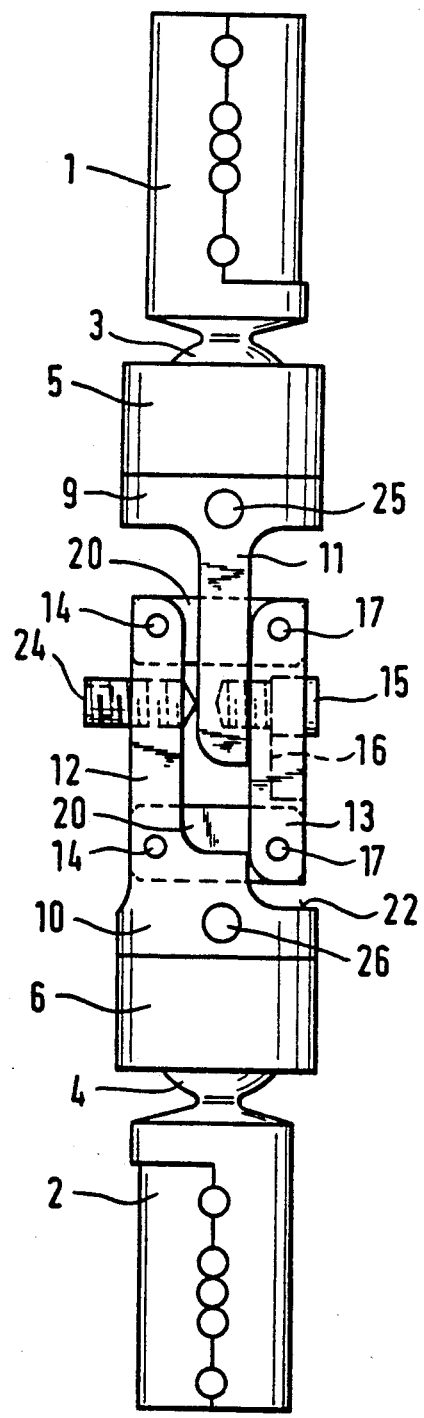
FIG. 1 is a side view of a fixation device incorporating the present invention.
Figure 2:
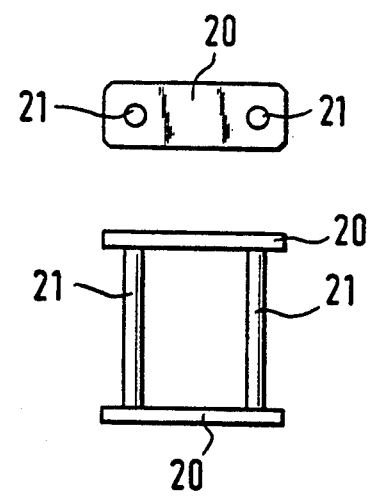
FIG. 2 is a plan view of the links for the parallelogram hinge.
Figure 3:
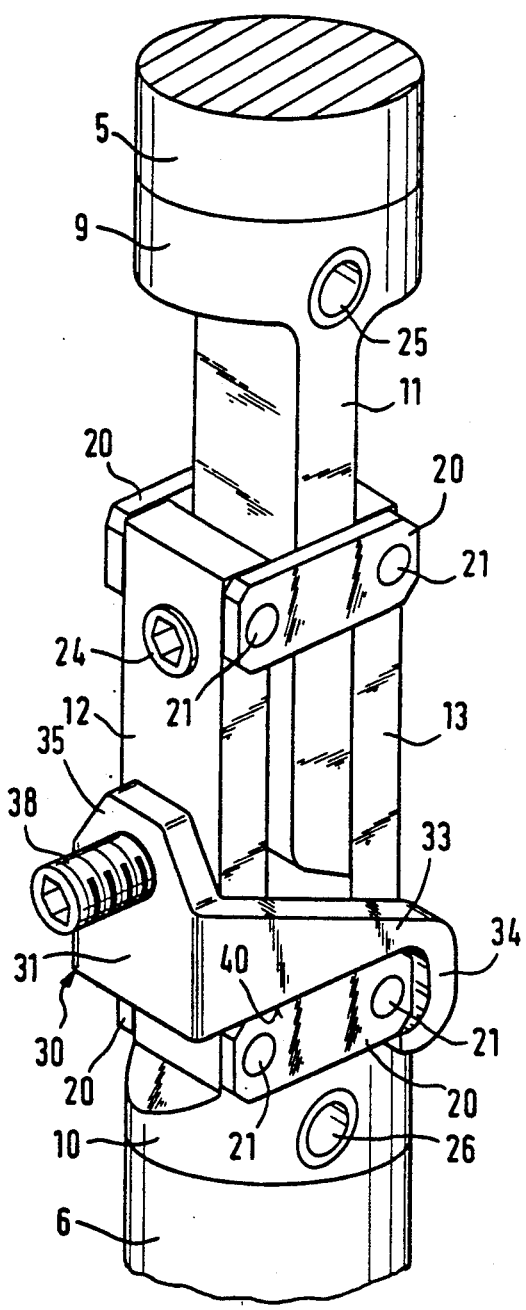
FIG. 3 is a perspective view of the fixation device according to FIG. 1 including a detachably mounted bracket.

Referring now to the drawings and in particular to FIG. 1 to 3 the fixation device comprises a pair of clamping members 1 and 2 for bolts (not shown) which are screwed in bone fragments above and below a fracture gap. One member each of the joint is defined by a ball 3 or respectively 4, which balls are integrally formed with the clamping members 1 and 2. Each ball 3, 4 is rotatably and fixedly supported in a second element 5 and 6 of the ball joint. The fixing unit is aligned and adjusted by means of the ball joints. Both clamps 1, 2 and the members 5, 6 are substantially cylindrical. A member 9 is connected to the joint member 5, which member 9 includes a substantially rectangular plate-like extension 11 integrally connected thereto. A plate 13 is connected to the extension 11 by means of a threaded bolt 15 which extends through an elongated bore 16 in the plate 13 and is screwed in a threaded bore of the extension 11. Accordingly the plate 13 can be longitudinally adjusted with respect to the member 9 whereupon the screw is tightened.

The opposite joint member 6 is detachably mounted on a member 10 including a rectangular extension plate 12. Both extension elements 12 and 13 are parallel to each other and are provided with bores 14 and 17 which are arranged opposite each other and equidistant relative to the longitudinal axis of the fixing unit. The bores 14 and 17 define the pivoting axis of the parallelogram hinge. Both hinge members are connected to each other by the links 20 shown in more detail in FIG. 2. The links 20 are connected to each other by pins 21, which are rotatably supported in the bores 14, 17.

The displacement of the hinge, i.e. the stroke of both members 10 and 11 is limited by an abutment 22. The gap between the abutment 22 of the member 10 and the forward face of the plate 13 amounts to several millimeters.

For tightening the fixing unit a pressure screw 24 is provided which is threaded in the extension plate 12 and contacts the extension 11.

Upon mounting the clamping elements 1, 2 on the bolts anchored in the bone fragments and longitudinally adjusting the fixing unit, the screw 15 is tightened. The hinge is then fixed by tightening the screw 24. To apply compressing forces on the fracture gap the screw 24 is untightened. Then the parallelogram hinge allows for both members 9 and 10 approaching each other while any substantial friction is eliminated and the relative guiding of both members is fully maintained. A driving tool for mounting and dismounting the ball joints may be inserted in openings 25 and 26 of the members 9 and 10. Additionally a position sensor (not shown) may be connected to the apertures 25 and 26 for measuring the relative approach of the bone fragments.

Figure 4:
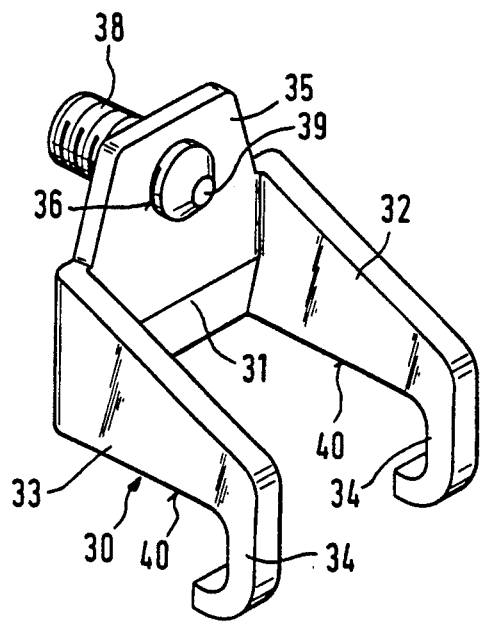
FIG. 4 is a perspective view of the bracket.

FIGS. 3 and 4 show the adjusting means which is formed as a bracket 30. The bracket 30 comprises a web 31 and a pair of arms 32 and 33 the ends 34 being hook-shaped. The web 31 has an extension 35 with a threaded bore 36 for inserting a screw 38, which has a rounded tip 39.

The bracket 30 is mounted on the hinge as shown in FIG. 3 such that the hook-shaped ends engage the lower pair of links 20. By screwing the bolt 38, which end 39 presses on the web 12, the bracket is adjusted. By screwing the screw 38 inwardly the members 9 and 10 are moved away from each other through the hook-shaped ends 34 so that a force is applied to the bone fragments to move them apart.

When the bracket 30 is inverted and mounted below the upper pair of links 20, wherein the hook-shaped ends 34 show upwardly and engage the upper pair of links 20 to the length of the hinge is decreased when the screw 38 is screwed in thus generating a tension force for pulling the bone fragments together in order to decrease the distance.

As indicated the bracket 30 acts as a double-armed lever. The one lever arm is defined by the web 31 and the extension 35 whereas the other lever arm 32, 33 has an edge 40 contacting the links 20 and the hook-shaped ends 34 engaging the link ends so that the bracket does not slide off.

Figure 5:
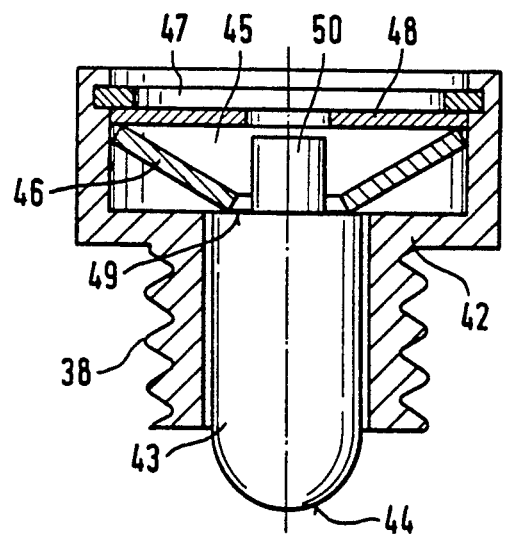
FIG. 5 is a section view of an adjusting screw to be mounted in the bracket.

FIG. 5 in conjunction with FIG. 3 shows a particular embodiment of a pressure screw 38 for limiting and indicating the compression and tension forces. A pin 43 is slidably supported in a sleeve 42 carrying an outer thread to be screwed into the threaded bore of the bracket 30. The rounded tip 44 of the pin 43 is pressed on the extension plate 12. The sleeve 42 is enlarged to define an annular space 45 at the end of the pin 43 to receive a Belleville spring (spring washer) 46 which is supported between a cover plate 48 connected to the sleeve 42 via a ring 47 and a shoulder 49 of the pin 43. The cover plate 48 has a central opening which may accommodate an extension 50 of the pin 43.

According to FIG. 5 the Belleville spring 46 is unloaded. When the sleeve 42 is screwed in the bracket, the pin 43 is urged on the plate 12 and the force exerted in screwing in is transferred through the Belleville spring 46 to the pin 43. Accordingly the pin 43 moves relative to the sleeve 42 and biases the Belleville spring 46. When the extension 50 enters the aperture in the cover plate 48 there is an indication of the motion performed by the bracket.

By selecting a variety of Belleville springs the compression or tension force may be limited to predetermined values. In screwing the device of FIG. 5 until the extension 50 is flush with the cover plate 48 the full bias of the Belleville spring is used and thus a predetermined pressure or tension force is reached. The variety of screws using different Belleville springs may be marked by colors for ease of handling.

Figure 6:
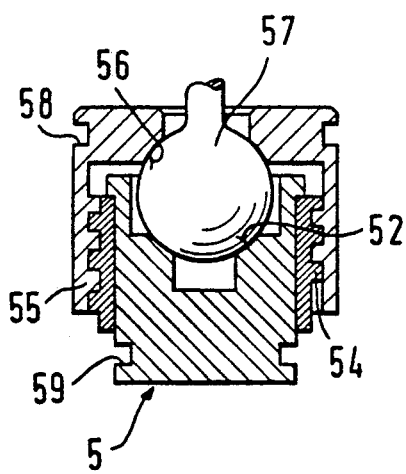
FIG. 6 is a section through a ball joint.

FIG. 6 shows a ball joint for connecting the fixing unit to the bone fragments. A ball 57 integrally formed on the clamping means illustrated in FIG. 1 is pressed to a spherical face 52 provided in the bore of the element 5 connected to the member 9. The element 5 is provided with an outer thread 54 which may be formed on separate semi-cylindrical shells made of steel when the element 5 is made of a soft material such as aluminum. A coupling nut 55 is screwed on the thread 54 to press its spherical face on the ball 57 for tightening it. Adjusting the ball joint is facilitated by wrenches carrying hooks engaging the recesses 58 and 59 in the coupling nut and the element 5 in order to prevent creating torque on the fixing unit, which may be painful to the patient.

Furthermore, it may be beneficial to the healing procedure when a pulsating pressure or tension is exerted on the fracture. For example, the pulsation is applied to the patient when resting. The screw 38 is replaced by a screw incorporating a hydraulic cylinder mounted thereon which is connected to a hydraulic device for generating a pulsating pressure on the pin 43. A pneumatic or electrical actuation may be provided as well.

Figure 7:
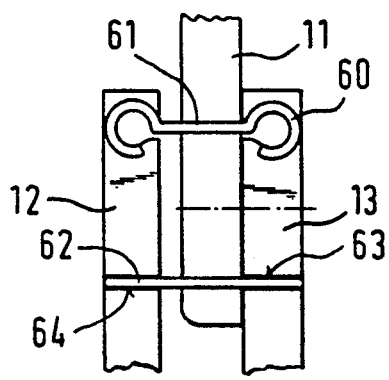
FIG. 7 shows part of the hinge incorporating blade springs.
Figure 12:
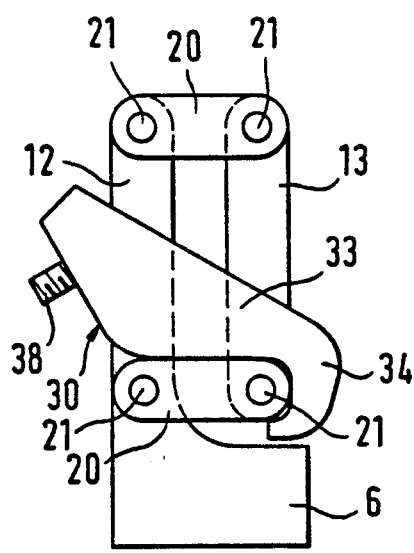
FIG. 12 is a schematic showing a force generated for pulling the bone fragments apart when a force is applied to the adjusting bracket in the position of FIG. 3.
Figure 13:
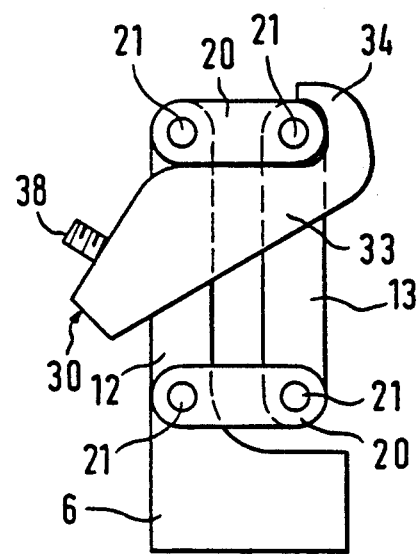
FIG. 13 is a schematic showing a force generated for pushing the bone fragments together when a force is applied to the adjusting bracket in an inverted position relative to FIG. 12.

According to FIG. 7 both members 12 and 13 of the hinge are biased in a centered position. Any displacement in either direction is then against the spring force which is beneficial to ossification. As shown in FIG. 7 at least one pair of the links of the hinge are replaced by blade springs 60 having bent ends for securing the blade springs in suitable openings of the members 12 and 13. With the ends fixed the linear portion 61 of the springs is bent when the hinge is displaced from the neutral position as shown. FIG. 7 shows a further blade spring 62 of which one end is secured to a groove 63 in element 13 with the other end freely engaging a groove 64 in the element 12. The spring 62 may be incorporated in the parallelogram hinge shown in FIGS. 1 to 3.

Another embodiment of a centered hinge device is shown in FIG. 8. A sleeve 70 is mounted on the joint member 5 and a rod 71 is mounted on the opposite joint member 6. The rod 71 extends into the sleeve 70. There is a pair of axially remote blade springs 72 for connecting the sleeve 70 to the rod 71. A top view of one of the blade springs 72 is shown in FIG. 9. The arms 73 of the spider spring may be offset to allow for the desired axial displacement of several millimeters. The springs resist any radial displacement between the tube 70 and the rod 71.

The spider spring shown in FIG. 9 may be replaced by a diskshaped spring. Longitudinal adjustment of the fixation device is possible by means of a bolt 75.

A still further embodiment is shown in FIG. 10 in which the annular space 75 between the sleeve 70 and the rod 71 is filled out by an elastomeric material adhering to the tube as well as to the rod. This material may be a silicon material. In the configuration shown the tube 70 and the rod 71 may be displaced longitudinally with respect to each other, while any substantial displacement is prevented. To improve the guidance, guiding ball members 76 supporting the rod 71 on the tube 70 may be provided on either end of the tube which ball members may be embedded in the elastomeric material.

In this embodiment the longitudinal adjustment of the fixation device is accomplished by an annular member 78 which is slidable on the sleeve 70 carrying the joint member 5.

FIG. 11 shows a multiple pivotal joint for mounting the fixation device to the bone fragments. Each pivotal joint comprises a tapered bolt 80 and a nut 82 is screwed on the threaded portion 81 of the bolt. The sleeve 70 is connected to the clamping means 1 by a pair of intermediate members 84 and 85. The joints allow for rotation in the axes x, y and z which axes intersect in the point s so that the arrangement allows for a three-dimensional adjustment. To reduce the axial length of the fixation device the clamping member 1 extends parallel and adjacent the tube 70.

What is claimed is:

1. A fixation device for externally adjusting a pair of bone fragments comprising:
    a pair of clamping means, each means anchored to each bone fragment,
    a pair of opposing members each of which is connected to each of said clamping means by a joint means, and
    a parallelogram hinge connecting the pair of opposing members to each other and enabling longitudinal displacement of the members relative to each other when the hinge is actuated.

2. The device of claim 1, wherein the longitudinal displacement of the members is limited to a range of several millimeters.

3. The device of claim 1, wherein each member comprises a seat for the joint means, and wherein the parallelogram hinge comprises a pair of substantially rectangular plates, one extending longitudinally from the seat of one member and the other being longitudinally adjustable and fixable on an extension of the seat of the other member, a plurality of links, each link pivotally connected to each substantially rectangular plate.

4. The device of claim 3, wherein the plates are provided with bores, said bores being equidistant with respect to the longitudinal axis of the plates, and further wherein the bores rotably support connecting pins which are connected to said links.

5. The device of claim 4, wherein an abutment is provided on one of the members to limit the longitudinal displacement of the hinge.

6. The device of claim 1, wherein the fixation device further comprises an adjusting means for actuating the parallelogram hinge in one of two opposing directions, wherein the adjusting means applies a pressure force to the bone fragments for moving them apart in one direction and applies a tension force for drawing the bone fragments together in the opposing direction.

7. The device of claim 6, wherein the adjusting means is a bracket which is mounted on the parallelogram hinge, said bracket defining a lever having two ends, one end of the lever engaging a link of the hinge, wherein by displacing the other end of the lever the parallelogram hinge is longitudinally adjusted by the end of the lever engaging the link.

8. The device of claim 7, wherein the bracket is mounted in a first position on the parallelogram hinge to cooperate with a link to apply the pressure force to the bone fragments and wherein the bracket is mounted in a second inverted position on the parallelogram hinge to cooperate with another link to apply the tension force on the bone fragments.

9. The device of claim 8, wherein the pressure and tension forces are generated by a screw mounted in the bracket enabling measurement of the forces.

10. The device of claim 9, wherein the screw comprises a threaded sleeve to be screwed in a threaded bore of the bracket and a sleeve pin slidably received in said sleeve, which pin is supported on said sleeve by a spring washer.

11. The device of claim 10, wherein a plurality of spring washers of varying bias forces are provided to generate predetermined pressure and tension forces and wherein marking means are provided to indicate when a predetermined bias is obtained.

12. The device of claim 9, wherein a pulsating pressure is applied to said bracket.

13. The device of claim 1, wherein the joint means is a ball joint for connecting said clamping means to one member each and includes a coupling nut cooperating with outer threads on a pair of semicircular shells surrounding one member for pressing a ball on the seat of said member.

14. A fixation device for externally adjusting a pair of bone fragments comprising:
    a pair of clamping means, each means anchored to each bone fragment,
    a pair of opposing members each of which is connected to each of said clamping means by a joint means, a parallelogram hinge connecting the pair of members to each other and enabling longitudinal displacement of the members relative to each other when the hinge is actuated, and at least a spring means for centering said parallelogram hinge in a predetermined position.

15. The device of claim 14, wherein said hinge comprises at least a pair of links and further wherein said links are blade springs.

16. The device of claim 14, wherein the hinge comprises a plurality of rigid links and a blade spring.

* * * * *